(12) United States Patent
Moor et al.

(10) Patent No.: US 9,119,367 B2
(45) Date of Patent: Sep. 1, 2015

(54) LETTUCE VARIETY 79-41 RZ

(75) Inventors: Cornelis Marinus Moor, Monster (NL); Egbert Carolus Johannes Smits, Zevenbergen (NL)

(73) Assignee: RIJK ZWAAN ZAADTEELT ENZAADHANDEL B.V., De Lier (NL)

( * ) Notice: Subject to any disclaimer, the term of this patent is extended or adjusted under 35 U.S.C. 154(b) by 358 days.

(21) Appl. No.: 13/482,582

(22) Filed: May 29, 2012

(65) Prior Publication Data

US 2012/0311732 A1     Dec. 6, 2012

Related U.S. Application Data

(60) Provisional application No. 61/491,564, filed on May 31, 2011.

(51) Int. Cl.
*A01H 5/12*     (2006.01)
*C12Q 1/68*     (2006.01)

(52) U.S. Cl.
CPC ........... *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 8,507,759 B2 * 8/2013 Moor et al. .............. 800/305

OTHER PUBLICATIONS

IBEB press release "New race of *Bremia lactucae* BI:27 identified and nominated", May 2010; Plantum NL (Dutch association for breeding, tissue culture, production and trade . . . .

Michelmore R. & Ochoa. O. "Breeding Crisphead Lettuce."In: California Lettuce Research Board, Annual Report 2005-2006, 2006, Salinas, California, pp. 55-68.

Schettini, T.M., Legg, E.J., Michelmore, R.W., 1991. Insensitivity to metalaxyl in California populations of *Bremia lactucae* and resistance of California lettuce cultivars . . . .

Van Ettekoven, K. et al., "Identification and denomination of 'new' races of *Bremia lactucae*," In: Lebeda, A. and Kristkova, E (eds.), Eucarpia Leafy Vegetables, 1999 . . . .

Van der Arend et al. "Identification and denomination of "new" races of *Bremia lactucae* in Europe by IBEB until 2002." In: Van Hintum, Th et al. (eds.), Eucarpia Leafy . . . .

* cited by examiner

*Primary Examiner* — Eileen B O Hara
(74) *Attorney, Agent, or Firm* — Vedder Price, P.C.; Thomas J. Kowalski; Deborah L. Lu

(57) ABSTRACT

The present invention relates to a *Lactuca sativa* seed designated 79-41 RZ, which may exhibit resistance to downy mildew (*Bremia lactucae* Regel.), currant-lettuce aphid (*Nasonovia ribis-nigri*) and Lettuce Mosaic Virus (LMV), and which may have light green, moderately glossy, deeply-incised, strongly undulated leaves. The present invention also relates to a *Lactuca sativa* plant produced by growing the 79-41 seed. The invention further relates to methods for producing the lettuce cultivar, represented by lettuce variety 79-41 RZ.

23 Claims, 2 Drawing Sheets

US 9,119,367 B2

LETTUCE VARIETY 79-41 RZ

RELATED APPLICATIONS AND INCORPORATION BY REFERENCE

This application which claims priority to U.S. provisional patent application Ser. No. 61/491,564 filed 31 May 2011.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety which may exhibit resistance against downy mildew (*Bremia lactucae*) races B1:1 to B1:27 and strain FR10.021, currant-lettuce aphid (*Nasonovia ribis-nigri*) and lettuce mosaic virus (LMV) as well as light green, moderately glossy, crisp, deeply-incised, strongly undulated, nicely-frilled leaves.

BACKGROUND OF THE INVENTION

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and chrysanthemum. Sativa is one of about 300 species in the genus *Lactuca*.

Lettuce cultivars are susceptible to a number of pests and diseases such as downy mildew (*Bremia lactucae*), currant-lettuce aphid (*Nasonovia ribis-nigri*) and lettuce mosaic virus (LMV). These diseases result in millions of dollars of lost lettuce crop throughout the world every year.

Downy mildew (*Bremia lactucae*) is highly destructive of lettuce that is grown at relatively low temperature and high humidity. Downy mildew is caused by a fungus, *Bremia lactucae*, which can be one of the following strains: NL1, NL2, NL4, NL5, NL6, NL7, NL10, NL12, NL13, NL14, NL15, NL16, B1:17, B1:18, B1:21, B1:22, B1:23, B1:24, B1:25, B1:26, B1:27 (Van Ettekoven, K. et al., "Identification and denomination of 'new' races of *Bremia lactucae*," In: Lebeda, A. and Kristkova, E (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151), Ca-V, Ca-VI, Ca-VII, Ca-VIII (Michelmore R. & Ochoa. O. "Breeding Crisphead Lettuce." In: California Lettuce Research Board, Annual Report 2005-2006, 2006, Salinas, Calif., pp. 55-68). Also new strains appear, which are overcoming resistance gene combinations in present varieties. An example is strain FR10.021 which is overcoming the Bremia-resistance in the variety "Expedition". New strains can be described by a sextetcode based on resistance test results on a set of 25 publicly available lettuce lines (IBEB press release May 2010. FR10.021 has sextetcode 63-31-62-03.

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Lettuce mosaic virus (LMV) mainly infects lettuce seeds, which is the primary way that the virus is introduced to lettuce in the fields, but also can infect numerous crops and weeds, thereby creating reservoirs of the virus. LMV also can be vectored by aphids, which spread the virus within a lettuce field and introduce it into lettuce fields from infected weeds and crops outside the field.

Of the various species of aphids that feed on lettuce, the currant-lettuce aphid (*Nasonovia ribis-nigri*) is the most destructive species because it feeds both on the leaves of the lettuce as well as deep in the heart of the lettuce, making it difficult to control with conventional insecticides. The lettuce aphid feeds by sucking sap from the lettuce leaves. Although direct damage to the lettuce may be limited, its infestation has serious consequences because the presence of aphids makes lettuce unacceptable to consumers.

Symptoms of lettuce mosaic virus vary greatly. Leaves of plants that are infected at a young stage are stunted, deformed, and (in some varieties) show a mosaic or mottling pattern. Such plants rarely grow to full size; head lettuce varieties infected early fail to form heads. Plants that are infected later in the growth cycle show a different set of symptoms. These plants may reach full size, but the older outer leaves turn yellow, twisted, and otherwise are deformed. On head lettuce, the wrapper leaves often will curve back away from the head and developing heads may be deformed. In some cases brown, necrotic flecks occur on the wrapper leaves.

Although several known lettuce cultivars exhibit resistance against disease, irrespective of lettuce type, many lettuce cultivars affected produce large leaves that, when cut to smaller size pieces generally result in a lot of cut surface resulting in a diminished shelf life with respect to wound-induced discolouration of these cut surfaces. Light green or 'blond' varieties are considered better tasting by consumers, due to their association with leaves from the heart of a lettuce plant, which are milder tasting as well as paler coloured than outer leaves.

Although several known lettuce cultivars can be harvested mechanically at young plant, i.e. babyleaf stage, no pest and disease resistant lettuce cultivars exist that can be harvested mechanically at mature stage and still provide leaf pieces that are of small, directly edible size and have an attractive green colour. Mechanical harvesting saves labour cost and improves labour conditions in comparison with commonly applied hand-harvesting methods.

There exists a need, therefore, for an mechanically harvestable lettuce variety which exhibits a combination of resistance against downy mildew (*Bremia lactucae*), currant-lettuce aphid (*Nasonovia ribis-nigri*) and Lettuce Mosaic Virus (LMV).

Citation or identification of any document in this application is not an admission that such document is available as prior art to the present invention.

SUMMARY OF THE INVENTION

It is the object of the invention to provide a new type of cutting/leaf lettuce, which may be suitable for mechanical harvest, and does not have or has reduced problems with downy mildew, currant-lettuce aphids, and Lettuce Mosaic Virus.

The present invention fulfils this need by providing a new cutting/leaf lettuce (*Lactuca sativa*) variety, designated 79-41 RZ. Lettuce variety 79-41 RZ exhibits a combination of traits including resistance to downy mildew (*Bremia lactucae* Regel) races B1:1 to B1:27 as well as strain FR10.021, currant-lettuce aphid (*Nasonovia ribis-nigri*) and Lettuce Mosaic Virus (LMV), as well as incised apical margin of the fourth leaf, light green to yellow green fourth leaf, deep incision of the margin, deeply dentate indentation of the margin, strong undulation of the apical margin, very light green mature leaf colour, and moderately glossy leaves.

The present invention provides seeds of lettuce cultivar 79-41 RZ, which have been deposited with the National Collections of Industrial, Marine and Food Bacteria (NCIMB) in Bucksburn, Aberdeen AB21 9YA, Scotland, UK and have been assigned NCIMB Accession No. 41837.

In one embodiment, the invention provides a lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, representative seed of which have been deposited under NCIMB Accession No. 41837.

In one embodiment, the invention provides a lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), black seeds, incised apical margin of the fourth leaf, light green to yellow green fourth leaf, deep incision of the margin, deeply dentate indentation of the margin, strong undulation of the apical margin, very light green mature leaf colour, moderately glossy leaves, none to slight blistering, thin leaves, moderately raised midrib, and very slow bolting, representative seed of which have been deposited under NCIMB Accession No. 41837.

In one embodiment, the invention provides a lettuce plant designated 79-41 RZ, representative seed of which have been deposited under NCIMB Accession No. 41837.

In an embodiment of the present invention, there also is provided parts of a lettuce plant of the invention, including parts of a lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, or parts of a lettuce plant having any of the aforementioned resistance(s) and a combination of traits including one or more morphological or physiological characteristics tabulated herein, including parts of lettuce variety 79-41 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts can come from include those wherein representative seed of which has been deposited under NCIMB Accession No. 41837.

In another embodiment there may be a plant grown from seeds, representative seed of which having been deposited under NCIMB Accession No. 41837. In a further embodiment there may be a plant regenerated from the above-described plant parts or regenerated from the above-described tissue culture. Advantageously such a plant has morphological and/or physiological characteristics of lettuce variety 79-41 RZ and/or of a plant grown from seed, representative seed of which having been deposited under NCIMB Accession No. NCIMB 41837—including without limitation such plants having all of the morphological and physiological characteristics of lettuce variety 79-41 RZ and/or of plant grown from seed, representative seed of which having been deposited under NCIMB Accession No. NCIMB 41837. Accordingly, in still a further embodiment, there is provided a lettuce plant having all of the morphological and physiological characteristics of lettuce variety 79-41 RZ, representative seed of which having been deposited under NCIMB Accession No. 41837. Such a plant can be grown from the seeds, regenerated from the above-described plant parts, or regenerated from the above-described tissue culture. A lettuce plant having any of the aforementioned resistance(s), a lettuce plant having any of the aforementioned resistance(s) and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In one embodiment, there is provided progeny of lettuce cultivar 79-41 RZ produced by sexual or vegetative reproduction, grown from seeds, regenerated from the above-described plant parts, or regenerated from the above-described tissue culture of the lettuce cultivar or a progeny plant thereof, representative seed of which having been deposited under NCIMB Accession No. 41837.

Progeny of the lettuce variety 79-41 RZ can be modified in one or more other characteristics, in which the modification may be a result of, for example and without limitation, mutagenesis or transformation with a transgene.

In still another embodiment, the present invention provides progeny of lettuce cultivar 79-41 RZ produced by sexual or vegetative reproduction, grown from seeds, regenerated from the above-described plant parts, or regenerated from the above-described tissue culture of the lettuce cultivar or a progeny plant thereof, in which the regenerated plant shows a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves.

In still a further embodiment, the invention may comprise a method of producing a hybrid lettuce seed which may comprise crossing a first parent lettuce plant with a second parent lettuce plant and harvesting the resultant hybrid lettuce seed, in which the first parent lettuce plant or the second parent lettuce plant may be a lettuce plant of the invention, e.g. a lettuce plant having a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, and one or more morphological or physiological characteristics tabulated herein, including a lettuce plant of lettuce cultivar 79-41 RZ, representative seed of which having been deposited under NCIMB 41837.

In another embodiment, the invention may comprise producing a lettuce plant having a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, which may comprise: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves. Advantageously the selfing and selection are repeated; for example at least once, or at least twice, thrice, four times, five times, six times or more, to produce F3 or F4 or F5 or F6 or subsequent progeny, especially as progeny from F2 can exhibit the aforementioned combination of traits, and can be desirable.

In still a further embodiment, the invention may comprise a method of producing a lettuce cultivar containing a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves.

The invention even further relates to a method of producing lettuce which may comprise: (a) cultivating to the vegetative plant stage a plant of lettuce variety 79-41 RZ, representative seed of which having been deposited under NCIMB Accession No. NCIMB 41837, and (b) harvesting lettuce leaves or heads from the plant. The invention further comprehends packaging the lettuce plants, heads or leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

Deposits

The Deposit with NCIMB Ltd, Ferguson Building, Craibstone Estate, Bucksburn, Aberdeen AB21 9YA, UK, on May 4, 2011, under deposit accession number NCIMB 41837 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION OF THE INVENTION

Figure 1:
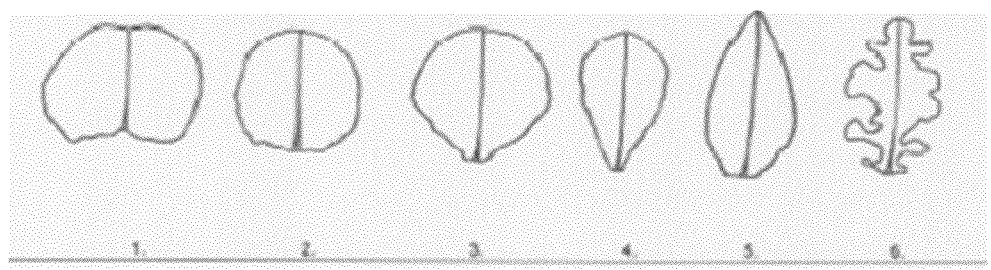
FIG. 1 is an illustration of six different shapes of the fourth leaf from a 20-day old seedling grown under optimal conditions.
Figure 2:
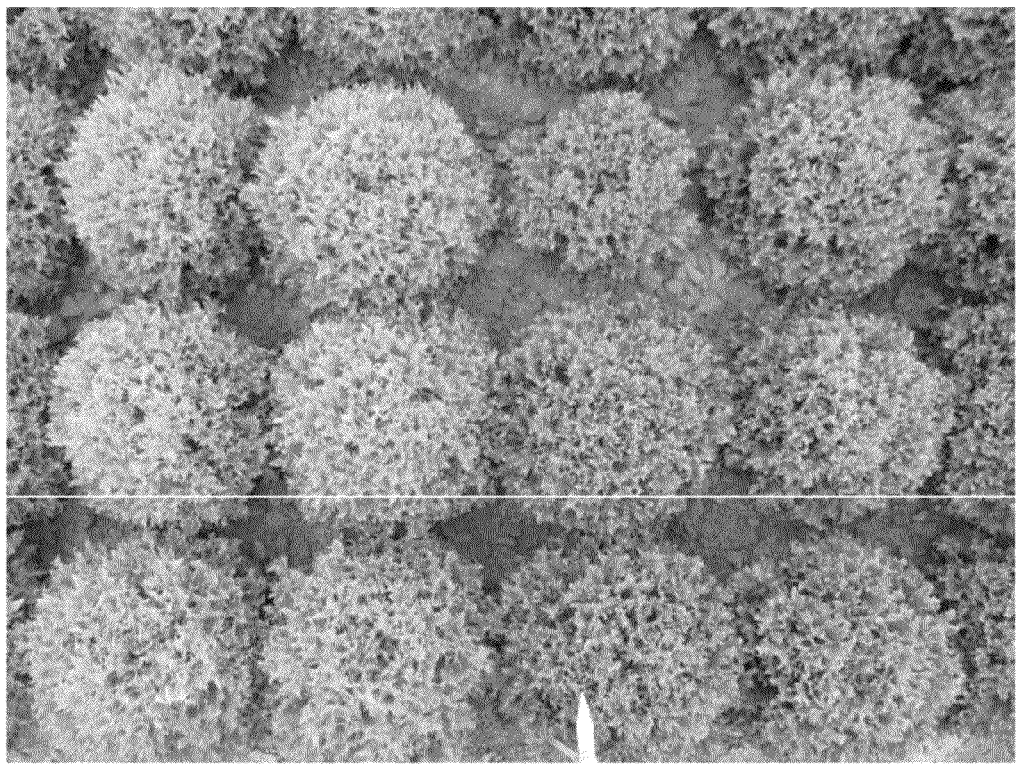
FIG. 2 is a comparison between 79-41 RZ and Expedition.

The invention provides methods and compositions relating to plants, seeds and derivatives of a new lettuce variety herein referred to as lettuce variety 79-41 RZ. Lettuce variety 79-41 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Lettuce variety 79-41 RZ was developed by crossing two varieties, 'Vivanto' and 'Explore', in a glasshouse in Fijnaart, the Netherlands in 2005, where the lettuce breeding is performed. The F1 resulting from this cross was grown under protected conditions. A population of F2 seed was obtained through self-pollination. When growing the F2 population in 2006, selection for multiple characteristics was performed, and specifically for Bremia-resistance and a desired leaf indentation. One F2 plant, 06P.35345 was selected and this plant was self-pollinated to obtain F3 seed, designated 07P.75370.

The F3 seed was sown in field conditions, still in 2006, and after a subsequent round of selection for multiple characteristics including Bremia-resistance and desired leaf-indentation, an F3 plant was selected, namely 07P.31722. The plant was self pollinated and F4 seed, 07P.90839, was produced. Subsequently, the F4 was sown in the field in 2007 as 07P.101324, and an F4 plant was selected from the population after selection for preferred characteristics including Bremia resistance and leaf indentation. Self pollination was performed, and F5 seed 08P.414298 was produced.

In 2008 and 2009 two more rounds of selection to optimize the uniformity of the line were done, resulting in F6 seed 09P.431518 and, after selecting and selfing the F6 plant 09F.40972, an F7 seedlot 09P.438393.

The seed from the F7 line 09P.438393 was established to be uniform, and multiplied in the glasshouse in Fijnaart, to obtain F8 seed lot 10R.615. After one final round of selfing, a confirmed stable and uniform F9 seed lot 11R.1574 was produced in 2010. 2500 seeds from this seed lot were deposited under Accession No. NCIMB 41837 on May 4, 2011.

In one embodiment, a plant of the invention has all the morphological and physiological characteristics of lettuce variety 79-41 RZ. These characteristics of a lettuce plant of the invention, e.g. variety 79-41 RZ, are summarized in Tables 1-3.

Next to the morphological and physiological characteristics mentioned in Tables 1-3, a plant of the invention also exhibits resistance to downy mildew (*Bremia lactucae* Regel.) races B1:1 to B1:27 as well as strain FR10.021, resistance against currant-lettuce aphid (*Nasonovia ribis-nigri* Mosley), and resistance against Lettuce Mosaic Virus (LMV).

As used herein resistance against *Bremia lactucae* Regel. is defined as the ability of a plant to resist infection by each of the various races, or strains, B1:1-27 as well as strain F10.021 of *Bremia lactucae* Regel. in all stages between the seedling stage and the harvestable plant stage. B1:1-27 or races B1:1 to B1:27 means strains NL1, NL2, NL4, NL5, NL6, NL7, NL10, NL12, NL13, NL14, NL15, NL16, B1:17, B1:18, B1:20, B1:21, B1:22, B1:23, B1:24, B1:25, B1:26, B1:27 (Van Ettekoven K, Van der Arend A J M, 1999 identification and denomination of 'new' races of *Bremia lactucae*. In: Lebeda A, Kristkova E (eds.) Eucarpia leafy vegetables '99. Palacky University, Olomouc, Czech Republic, 1999: 171-175; Van der Arend, A. J. M., Gautier, J., Guenard, M., Michel, H., Moreau, B., de Ruijter, J., Schut, J. W. and de Witte, I. (2003). Identification and denomination of 'new' races of *Bremia lactucae* in Europe by IBEB until 2002. In: Eucarpia leafy vegetables 2003. Proceedings of the Eucarpia Meeting on leafy vegetables genetics and breeding. Noorwijkerhout, The Netherlands. Eds. Van Hintum T., Lebeda A., Pink D., Schut J. pp 151-160; Van der Arend A J M, Gautier J, Grimault V, Kraan P, Van der Laan R, Mazet J, Michel H, Schut J W, Smilde D, De Witte I (2006) Identification and denomination of "new" races of *Bremia lactucae* in Europe by IBEB until 2006; incorporated herein by reference). Strain FR10.021 has sextetcode 63-31-62-03 and the variety "Expedition" is FR10.021-susceptible.

Resistance typically is tested by two interchangeable methods, described by Bonnier, F. J. M. et al. (Euphytica, 61(3): 203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against *Nasonovia ribis-nigri* (Mosley), or currant-lettuce aphid, is defined as the plant characteristic which results in a non-feeding response of a *Nasonovia ribis-nigri* aphid of the Nr:0-biotype on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference).

Resistance is tested by spreading at least ten aphids of biotype Nr:0 on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Daylength is kept at 18 hours by assimilation lights.

As used herein, resistance against Lettuce Mosaic Virus (LMV) is defined as the ability of the plant to grow normally after LMV infection and to inhibit the virus transmission via seed. Resistance is tested by mechanical inoculation of young plants in a climate cell or a greenhouse, as described by Pink, D. A. C. et al. (Plant Pathology, 41(1):5-12, 1992), incorporated herein by reference. Inoculated resistant plants grow just as well as uninoculated plants and show no chlorosis or mosaic symptoms. The LMV isolate which is used for testing is Ls-1 (International Union for the Protection of New Varieties of Plants [UPOV]), Guidelines for the conduct of tests for distinctness, uniformity and stability; lettuce (*Lactuca sativa* L.), 2002, p. 35; incorporated herein by reference).

As used herein, an acceptable product for consumers and/or the lettuce processing industry is defined as the absence of tipburn, a high number of relatively uniform-sized, three-dimensional, i.e. non-flat, lettuce leaf pieces with small-sized cut surfaces, which have preferably been obtained by mechanical harvesting.

Embodiments of the inventions advantageously have one or more, and most advantageously all, of these characteristics.

In the Tables that follow, the traits and characteristics of the *Lactuca sativa* L. cutting/leaf lettuce plant having the designation 79-41 RZ are given compared to the most similar variety, referred to as "Expedition" and a standard regional check variety, referred to as "Grand Rapids".

In Table 1, the seed color, cotyledon shape and characteristic of the fourth leaf of "79-41" is compared with "Expedition" and "Grand Rapids". RHS=Royal Horticultural Society Colour Chart, 5$^{th}$ Edition, London, UK.

TABLE 1

| Character | "79-41" | "Expedition" | "Grand Rapids" |
|---|---|---|---|
| Plant Type | cutting/leaf | cutting/leaf | cutting/leaf |
| Seed color | Black (Grey Brown) | White (Silver Gray) | Black (Grey Brown) |
| Cotyledon Shape | Spatulate | Spatulate | Intermediate |
| Shape of the Fourth Leaf | Elongated | Elongated | Elongated |
| Fourth Leaf Apical Margin | Incised | Incised | Slightly Dentate |
| Fourth Leaf Basal Margin | Very Coarsely Dentate | Very Coarsely Dentate | Coarsely Dentate |
| Undulation | Slight | Slight | Medium |
| Green Color | Light Green to Yellow Green (RHS 144B) | Medium Green | Light Green to Yellow Green (RHS 144B) |
| Anthocyanin Distribution | Absent | Absent | Absent |
| Rolling of Fourth Leaf | Present | Present | Present |
| Cupping of Fourth Leaf | Uncupped | Uncupped | Uncupped |
| Reflexing of Fourth Leaf | Apical Margin | Apical Margin | Apical Margin |

In Table 2, the mature leaf and head characteristics of "79-41" are compared with "Expedition" and "Grand Rapids" in a Spring trial in Fijnaart in 2011.

TABLE 2

| Character | "79-41" | "Expedition" | "Grand Rapids" |
|---|---|---|---|
| Green Color | Very Light Green (RHS 144A) | Medium Green (RHS 146B) | Light Green to Yellow Green (RHS 144B) |
| Margin Incision Depth | Deep | Deep | Moderate |
| Margin Indentation | Deeply Dentate | Deeply Dentate | Shallowly Dentate |
| Undulations of the Apical Margin | Strong | Strong | Moderate |
| Anthocyanin Distribution | Absent | Absent | Absent |
| Leaf Size | Medium | Medium | Medium |
| Leaf Glossiness | Moderate | Dull | Moderate |
| Leaf Blistering | Absent/slight | Absent/slight | Moderate to strong |
| Leaf Thickness | Thin | Thin | Intermediate |
| Trichomes | Absent | Absent | Absent |
| Head Shape | Non-heading | Non-heading | Elongate |

As used herein, a dull upper side of a mature leaf is characterized by absence of gloss of the upper side of a mature leaf. For comparison the standard variety Vanguard can be used. As used herein, a moderately glossy leaf is characterised by the presence of a moderately shiny gloss of the upper side of a mature leaf. For comparison the standard variety Salinas can be used.

In Table 3, the characteristics of the butt, core and bolter plant "79-41" are compared with "Expedition" and "Grand Rapids".

TABLE 3

| Character | "79-41" | "Expedition" | "Grand Rapids" |
|---|---|---|---|
| Butt Shape | Rounded | Rounded | Rounded |
| Butt Midrib | Moderately Raised | Moderately Raised | Prominently Raised |
| Bolting Class | Very Slow | Very Slow | Slow |
| Bolter Leaves | Curved | Curved | Curved |
| Bolter Margin | Dentate | Dentate | Dentate |

In an embodiment, the invention relates to lettuce plants that has all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into the plant of the invention, being a plant of lettuce variety 79-41 RZ, by genetic transformation techniques; and, such plants of lettuce variety 79-41 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of lettuce variety 79-41 RZ or may, alternatively, be used for the preparation of transgenes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus. A vector can be introduced into lettuce cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of lettuce variety 79-41 RZ.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked, by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including lettuce plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from lettuce (psaD, psaF, psaE, PC, FNR, atpC, atpD, cab, rbcS) (see U.S. Pat. No. 7,161,061), the CAB-1 promoter from lettuce (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 79-41 RZ. Non-limiting examples of particular genes and corresponding phenotypes one may choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed lettuce and/or methods of transforming lettuce or lettuce plant cells, and techniques from these US patents, as well as promoters, vectors, etc., may be employed in the practice of this invention to introduce exogenous nucleic acid sequence(s) into a plant of lettuce variety 79-41 RZ (or cells thereof), and exemplify some exogenous nucleic acid sequence(s) which can be introduced into a plant of lettuce variety 79-41 RZ (or cells thereof) of the invention, as well as techniques, promoters, vectors etc., to thereby obtain further plants of lettuce variety 79-41 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material comprises inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on lettuce being recognized as a plant that can be regenerated from cultured cells or tissue).

Also, the invention comprehends methods for producing a seed of a "79-41 RZ"-derived lettuce plant comprising (a) crossing a plant of lettuce variety 79-41 RZ, representative seed of which having been deposited under NCIMB Accession No. NCIMB 41837, with a second lettuce plant, and (b) whereby seed of a "79-41 RZ"-derived lettuce plant form (e.g., by allowing the plant from the cross to grow to producing seed). Such a method can further comprise (c) crossing a plant grown from "79-41 RZ"-derived lettuce seed with itself or with a second lettuce plant to yield additional "79-41 RZ"-derived lettuce seed, (d) growing the additional "79-41 RZ"-derived lettuce seed of step (c) to yield additional "79-41 RZ"-derived lettuce plants, and (e) repeating the crossing and growing of steps (c) and (d) to generate further "79-41 RZ"-derived lettuce plants.

The invention additionally provides a method of introducing a desired trait into a plant of lettuce variety 79-41 RZ comprising: (a) crossing a plant of lettuce variety 79-41 RZ, representative seed of which having been deposited under NCIMB Accession No. NCIMB 41837, with a second lettuce plant that comprises a desired trait to produce F1 progeny; (b) selecting an F1 progeny that comprises the desired trait; (c) crossing the selected F1 progeny with a plant of lettuce variety 79-41 RZ, to produce backcross progeny; (d) selecting backcross progeny comprising the desired trait and the physiological and morphological characteristic of a plant of lettuce variety 79-41 RZ; and, optionally, (e) repeating steps (c) and (d) one or more times in succession to produce selected fourth or higher backcross progeny that comprise the desired trait and all of the physiological and morphological characteristics of a plant of lettuce variety 79-41 RZ, when grown in the same environmental conditions. The invention, of course, includes a lettuce plant produced by this method.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 79-41 RZ, representative seed of which having been deposited under NCIMB Accession No. NCIMB 41837, is used in backcrossing, offspring retaining the combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves are progeny within the ambit of the invention. Backcrossing methods can be used with the present invention to improve or introduce a characteristic into a plant of the invention, being a plant of lettuce variety 79-41 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of lettuce variety 79-41 RZ, representative seed of which has been deposited under NCIMB Accession No. NCIMB 41837, or a first generation progeny thereof, comprising obtaining a sample of nucleic acids from said plant and detecting in said nucleic acids a plurality of polymorphisms. This method can additionally comprise the step of storing the results of detecting the plurality of polymorphisms on a computer readable medium. The plurality of polymorphisms are indicative of and/or give rise to the expression of the morphological and physiological characteristics of lettuce variety 79-41 RZ.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container comprising one or more plants of the invention, or one or more lettuce plants derived from a plant of the invention, in a growth substrate for harvest of leaves from the plant in a domestic environment. This way the consumer can pick very fresh leaves for use in salads. More generally, the invention includes one or more plants of the invention or one or more plants derived from lettuce of the invention, wherein the plant is in a ready-to-harvest condition, including with the consumer picking his own, and further including a container comprising one or more of these plants.

The invention is further described by the following numbered paragraphs:

1. Lettuce plant exhibiting a combination of traits including resistance against downy mildew (*Bremia lactucae*) races B1:1 to B1:27 as well as strain FR19.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, representative seed of which having been deposited under NCIMB Accession No. 41837.

2. Lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), black seeds, incised apical margin of the fourth leaf, light green to yellow green fourth leaf, deep incision of the margin, deeply dentate indentation of the margin, strong undulation of the apical margin, very light green mature leaf colour, moderately glossy leaves, none to slight blistering, thin leaves, moderately raised midrib, and very slow bolting, representative seed of which having been deposited under NCIMB Accession No. 41837.

3. Lettuce plant designated RZ 79-41, representative seed of which having been deposited under NCIMB Accession No. 41837.

4. Seed of the plant of paragraph 1.

5. Parts of the plant of paragraph 1, wherein said parts of the plant are suitable for sexual reproduction.

6. Parts of the plant as claimed in paragraph 5, said parts selected from the group consisting of microspores, pollen, ovaries, ovules, embryo sacs and egg cells.

7. Parts of the plant of paragraph 1, wherein said parts of the plant are suitable for vegetative reproduction.

8. Parts as claimed in paragraph 7, said parts selected from the group consisting of cuttings, roots, stems, cells and protoplasts.

9. A tissue culture of regenerable cells from the lettuce plant of paragraph 1.

10. A tissue culture as claimed in paragraph 9, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

11. Progeny of a lettuce plant of paragraph 1.

12. Progeny as claimed in paragraph 11, wherein said progeny is produced by sexual or vegetative reproduction of said lettuce plant, and wherein said progeny exhibits a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves.

13. Progeny of a lettuce plant of paragraph 3, having all the morphological and physiological characteristics of the lettuce plant of paragraph 3, representative seed of which having been deposited under NCIMB Accession NO. 41837 wherein as found in lettuce variety RZ 79-41, representative seed of which having been deposited under NCIMB Accession No. 41837.

14. Progeny of a lettuce plant of paragraph 1, representative seed of which having been deposited under NCIMB Accession 41837, and is modified in one or more other characteristics.

15. Progeny as claimed in paragraph 14, wherein the modification is effected by mutagenesis.

16. Progeny as claimed in paragraph 14, wherein the modification is effected by transformation with a transgene.

17. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of paragraph 1.

18. A method of producing a lettuce cultivar containing a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, and, selfing said selected F2-plants to produce F3 progeny seed; selecting F3-plants for exhibiting resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, optionally followed by more selfing and selection steps.

19. A method for producing lettuce leaves as a fresh vegetable comprising packaging leaves of a plant of paragraph 1.

20. A method for producing lettuce leaves as a processed food comprising processing leaves of a plant of paragraph 1.

21. One or more lettuce plants of paragraph 1, in a container, for harvest of leaves.

22. Lettuce plant having morphological and/or physiological characteristics of a lettuce plant, representative seed of which having been deposited under NCIMB Accession No. 41837.

23. Lettuce plant of paragraph 22 having all the morphological and physiological characteristics of the lettuce plant, representative seed of which having been deposited under NCIMB Accession No. 41837.

24. A method of introducing a desired trait into a plant of lettuce variety 79-41 RZ comprising: (a) crossing a plant of lettuce variety 79-41 RZ, representative seed of which having been deposited under NCIMB Accession No. NCIMB 41837, with a second lettuce plant that comprises the desired trait to produce F1 progeny; (b) selecting an F1 progeny that comprises the desired trait; (c) crossing the selected F1 progeny with a plant of lettuce variety 79-41 RZ, to produce backcross progeny and (d) selecting backcross progeny comprising the desired trait and the physiological and morphological characteristic of a plant of lettuce variety 79-41 RZ; when grown in the same environmental conditions.

25. The method of paragraph 24 further comprising (e) repeating steps (c) and (d) one or more times in succession to produce selected fourth or higher backcross progeny that comprise the desired trait and all of the physiological and morphological characteristics of a plant of lettuce variety 79-41 RZ, when grown in the same environmental conditions.

26. A lettuce plant produced by the method of paragraph 24 or 25.

27. A method for producing a seed of a 79-41 RZ-derived lettuce plant comprising (a) crossing a plant of lettuce variety 79-41 RZ, representative seed of which having been deposited under NCIMB Accession No. NCIMB 41837, with a second lettuce plant, and (b) whereby seed of a 79-41 RZ-derived lettuce plant form.

28. The method of paragraph 27 further comprising (c) crossing a plant grown from 79-41 RZ-derived lettuce seed with itself or with a second lettuce plant to yield additional 79-41 RZ-derived lettuce seed, (d) growing the additional 79-41 RZ-derived lettuce seed of step (c) to yield additional 79-41 RZ-derived lettuce plants, and (e) repeating the crossing and growing of steps (c) and (d) to generate further 79-41 RZ-derived lettuce plants.

29. A method of determining the genotype of a plant of lettuce variety 79-41 RZ, representative seed of which has been deposited under NCIMB Accession No. NCIMB 41837, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 79-41 RZ.

30. The method of paragraph 29 additionally comprising the step of storing the results of detecting the plurality of polymorphisms on a computer readable medium, or transmitting the results of detecting the plurality of polymorphisms.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, representative seed of which having been deposited under NCIMB Accession No. 41837.

2. The lettuce plant of claim 1, wherein the plant further exhibits a combination of traits including black seeds, none to slight blistering, thin leaves, moderately raised midrib, and very slow bolting.

3. A seed of the plant of claim 1.

4. A part of the plant of claim 1, wherein said parts of the plant is suitable for sexual reproduction or wherein said part of the plant is suitable for sexual reproduction and wherein said comprises a microspore-s, pollen, an ovary, an ovule, an embryo sac or an egg cell or wherein said parts of the plant is suitable for vegetative reproduction or wherein said part of the plant is suitable for vegetative reproduction and wherein said part comprises a cutting, a root, a stem, a cell or a protoplast.

5. A tissue culture of regenerable cells from the lettuce plant of claim 1, optionally wherein said cells or protoplasts of the tissue culture are derived from a tissue selected from the group consisting of leaves, pollen, embryos, cotyledon, hypocotyls, meristematic cells, roots, root tips, anthers, flowers, seeds and stems.

6. Progeny of a lettuce plant of claim 1, wherein the progeny exhibits the combination of traits of the lettuce plant of claim 1.

7. Progeny as claimed in claim 6, wherein said progeny is produced by sexual or vegetative reproduction of said lettuce plant, and wherein said progeny exhibits a combination of traits including resistance against downy mildew (*Bremia lactucae*) races B1:1 to B1:27 as well as strain FR10.021, resistance against currant-lettuce aphid (*Nasonovia ribisnigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf color, and moderately glossy leaves.

8. Progeny of a lettuce plant of claim 1, representative seed of which having been deposited under NCIMB Accession 41837, wherein the progeny exhibits the combination of traits of the lettuce plant of claim 1 and is further modified in one or more other characteristics.

9. Progeny as claimed in claim 8, wherein the modification is effected by mutagenesis or wherein the modification is effected by transformation with a transgene.

10. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1 or a method of producing a lettuce cultivar containing a combination of traits including resistance against downy mildew (*Bremia lactucae*) races B1:1 to B1:27 as well as strain FR10.021, resistance against currant-lettuce aphid (Nasonovia ribis-nigri), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, and, selfing said selected F2-plants to produce F3 progeny seed; selecting F3-plants for exhibiting resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves, optionally followed by more selfing and selection steps.

11. A method for producing lettuce leaves as a fresh vegetable comprising packaging leaves of a plant of claim 1.

12. A method for producing lettuce leaves as a processed food comprising processing leaves of a plant of claim 1.

13. A lettuce plant having morphological and/or physiological characteristics of a lettuce plant, representative seed of which having been deposited under NCIMB Accession No. 41837, and wherein said lettuce plant exhibits a combination of traits including resistance against downy mildew (*Bremia lactucae*) races B1:1 to B1:27 as well as strain FR10.021, resistance against currant-lettuce aphid (*Nasonovia ribisnigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf color, and moderately glossy leaves.

14. A lettuce plant of claim 13 having all the morphological and physiological characteristics of the lettuce plant, representative seed of which having been deposited under NCIMB Accession No. 41837.

15. A method of introducing a desired trait into a plant of lettuce variety 79-41 RZ comprising: (a) crossing a plant of lettuce variety 79-41 RZ, representative seed of which having been deposited under NCIMB Accession No. NCIMB 41837, with a second lettuce plant that comprises the desired trait to produce F1 progeny; (b) selecting an F1 progeny that comprises the desired trait; (c) crossing the selected F1 progeny with a plant of lettuce variety 79-41 RZ, to produce backcross progeny and (d) selecting backcross progeny comprising the desired trait and the physiological and morphological characteristics of a plant of lettuce variety 79-41 RZ, when grown in the same environmental conditions.

16. The method of claim 15 further comprising (e) repeating steps (c) and (d) one or more times in succession to produce selected fourth or higher backcross progeny that comprise the desired trait and all of the physiological and morphological characteristics of a plant of lettuce variety 79-41 RZ, when grown in the same environmental conditions.

17. A lettuce plant produced by the method of claim 15.

18. A method for producing a seed of a 79-41 RZ-derived lettuce plant comprising (a) crossing a plant of lettuce variety 79-41 RZ, representative seed of which having been deposited under NCIMB Accession No. NCIMB 41837, with a second lettuce plant, and (b) whereby seed of a 79-41 RZ-derived lettuce plant form.

19. The method of claim 18 further comprising (c) crossing a plant grown from 79-41 RZ-derived lettuce seed with itself or with a second lettuce plant to yield additional 79-41 RZ-derived lettuce seed, (d) growing the additional 79-41 RZ-derived lettuce seed of step (c) to yield additional 79-41 RZ-derived lettuce plants, and (e) repeating the crossing and growing of steps (c) and (d) to generate further 79-41 RZ-derived lettuce plants.

20. A method of determining the genotype of a plant of lettuce variety 79-41 RZ, representative seed of which has been deposited under NCIMB Accession No. NCIMB 41837, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 79-41 RZ and optionally additionally comprising the step of storing the results of detecting the plurality of polymorphisms on a computer readable medium, or transmitting the results of detecting the plurality of polymorphisms.

21. A lettuce plant designated 79-41 RZ, representative seed of which having been deposited under NCIMB Accession No. 41837.

22. Progeny of a lettuce plant of claim 21, having all the morphological and physiological characteristics of the lettuce plant of claim 21, representative seed of which having been deposited under NCIMB Accession NO. 41837.

23. A lettuce plant exhibiting a combination of traits including resistance against downy mildew (*Bremia lactucae*) races B1:1 to B1:27 as well as strain FR10.021, resistance against currant-lettuce aphid (*Nasonovia ribis-nigri*), resistance against Lettuce Mosaic Virus (LMV), incised apical margin of the fourth leaf, light green to yellow green fourth leaf, deep incision of the margin, deeply dentate indentation of the margin, strong undulation of the apical margin, very light green mature leaf colour, and moderately glossy leaves and having genetic material for so exhibiting the combination of traits; wherein the genetic information is as contained in a plant, representative seed of which having been deposited under NCIMB Accession No. 41837.

* * * * *

UNITED STATES PATENT AND TRADEMARK OFFICE
CERTIFICATE OF CORRECTION

| | |
|---|---|
| PATENT NO. | : 9,119,367 B2 |
| APPLICATION NO. | : 13/482582 |
| DATED | : September 1, 2015 |
| INVENTOR(S) | : Cornelis Marinus Moor et al. |

It is certified that error appears in the above-identified patent and that said Letters Patent is hereby corrected as shown below:

ON THE TITLE PAGE, the Assignee name is incorrectly listed as:
Item 73 Assignee: RIJK ZWAAN ZAADTEELT ENZAADHANDEL B.V., De Lier (NL)

Please correct the Assignee name to read:
Item 73 Assignee: RIJK ZWAAN ZAADTEELT EN ZAADHANDEL B.V., De Lier (NL)

Signed and Sealed this
Fifteenth Day of March, 2016

Michelle K. Lee
*Director of the United States Patent and Trademark Office*